(12) United States Patent
Ravazzolo

(10) Patent No.: US 8,645,156 B2
(45) Date of Patent: Feb. 4, 2014

(54) INVENTORY AND PATIENT MANAGEMENT SYSTEM

(75) Inventor: Kenneth George Ravazzolo, San Diego, CA (US)

(73) Assignee: ResMed Limited, Bella Vista (AU)

(*) Notice: Subject to any disclaimer, the term of this patent is extended or adjusted under 35 U.S.C. 154(b) by 1681 days.

(21) Appl. No.: 11/674,756

(22) Filed: Feb. 14, 2007

(65) Prior Publication Data
US 2007/0198357 A1 Aug. 23, 2007

Related U.S. Application Data

(60) Provisional application No. 60/775,782, filed on Feb. 23, 2006.

(51) Int. Cl.
*G06Q 50/00* (2012.01)
*G06Q 10/00* (2012.01)

(52) U.S. Cl.
USPC .................................... 705/2; 705/3

(58) Field of Classification Search
USPC ......................................................... 705/2
See application file for complete search history.

(56) References Cited

U.S. PATENT DOCUMENTS

| | | | | |
|---|---|---|---|---|
| 3,575,586 A | * | 4/1971 | Kroll | 235/378 |
| 5,602,377 A | * | 2/1997 | Beller et al. | 235/462.15 |
| 5,732,401 A | * | 3/1998 | Conway | 705/29 |
| 6,196,970 B1 | * | 3/2001 | Brown | 600/300 |

OTHER PUBLICATIONS

Fry, Mascal: RFID Tracking of Patients, Staff and Equipment to Enhance Hospital Response to Mass Casualty Events, 2005, AMIA Annu Symp Proc.; 261-265.*

* cited by examiner

*Primary Examiner* — Tran Nguyen
(74) *Attorney, Agent, or Firm* — Nixon & Vanderhye, PC

(57) ABSTRACT

A system and/or method for managing patients and products used in the treatment of their sleep-disordered breathing (SDB) is provided. A barcode scanner preferably scans product data and wirelessly communicates it to a database for use in an inventory management system for tracking and generating product and patient information for Obstructive Sleep Apnea (OSA) treatment, for example, when receiving items into stock, dispensing products, returning loaned, rented, and/or defective products, etc. Custom patient reminders, notes, reports, and the like may be generated automatically based on the scanned data.

24 Claims, 10 Drawing Sheets

INVENTORY AND PATIENT MANAGEMENT SYSTEM

CROSS-REFERENCE TO RELATED APPLICATION

This application claims the benefit of Provisional Application No. 60/775,782, filed Feb. 23, 2006, the entire contents of which is hereby incorporated herein by reference.

FIELD OF THE INVENTION

The present invention relates to a system and/or method for managing patients and products used in the treatment of sleep-disordered breathing (SDB). In particular, the present invention relates to a barcode scanner which preferably scans product data and wirelessly communicates it to a database for use in an inventory management system for tracking and generating product and patient information for Obstructive Sleep Apnea (OSA) treatment.

BACKGROUND OF THE INVENTION

Obstructive Sleep Apnea (OSA) and other dangerous sleep-disordered breathing (SDB) conditions affect thousands worldwide. Numerous techniques have emerged for the treating SDB, including, for example, the use of Continuous Positive Airway Pressure (CPAP) devices, which continuously provide pressurized air or other breathable gas to the entrance of a patient's airways via a patient interface (e.g. a mask) at a pressure elevated above atmospheric pressure, typically in the range 3-20 cm $H_2O$. Typically, patients suspected of suffering from an SDB register with a certified sleep laboratory where sleep technicians fit patients with numerous data collectors and monitor their sleep activity over a given period. If a diagnosis of SDB is, the patient is referred to a provider of products used in the treatment for SDB. These providers typically are referred to as durable medical equipment (DME) and/or home medical equipment (HME) providers.

There are many processes associated with the dispensing of products used in the treatment of SDB. For example, set-up forms, rental and loaner agreements and other documents are created; patient notes, including device settings are created; follow-up reminders used for compliance and supplies replacement are created; etc. Conventionally, these processes rely on hand-writing and transcribing. For example, although the provider keeps track of, for example, their inventory (e.g. how many CPAP devices are in stock, how many are on loan and/or rented, etc.), which patients receive which treatment device, timely patient follow-ups (e.g. for routine monitoring of treatment progress, maintenance for devices, etc.), and the like, they often do so in whole or in part by hand. Where computerized systems are involved, they too require manual entry of numerous parameters.

Thus, numerous problems are inherent in these processes for dispensing products and tracking both products and patients. For example, providers risk running out of stock of particular devices. Without adequate and accurate records, providers also may risk losing rental and loaner units. When loaned and/or rented devices are returned, improper recordation may erroneously report that they are still outstanding, missing, etc.

Multiple types of inventories create further problems. For example, a provider may need to track whether it is dispensing a device that is, for example, new, used, rental, loaner, donated, etc. The varied types of devices and the various different reporting requirements associated therewith add a further level of complication to the system. These and other problems may be compounded by the ease with which serial numbers and/or other identifying information may be transposed. Thus, even when theoretically adequate and accurate records are kept, innocent human error could lead to these and other problems. For example, patients may be issued the incorrect device, etc.

Similar problems exist with regard to tracking patients. For example, most providers typically know when devices are issued when follow-ups will be required. However, many conventional systems, for example, do not track such information and do not generate reminders. As another example, routine patient notes and forms, including set-up forms, rental agreements, loaner agreements, etc., the contents of which are standard, must be created by hand. As a result, considerable time, effort, and money may be wasted.

Some SDB product manufacturers have implemented barcode technology to quickly and accurately track products by serial and lot numbers by default because they ship their products through commercial carriers, such as, for example, Federal Express, UPS, etc. However, these conventional systems typically use proprietary concatenated barcodes. These barcodes are not industry-standard barcodes and therefore require additional hardware and/or software power, for example, to parse and further manipulate incoming data. These systems typically are not integrated with patient management information.

Typically, providers have implemented patient management billing systems. Many of these systems include an inventory module as well. However, these systems typically are of a generic nature and do not accommodate the unique aspects of managing patients, product and inventory associated with SDB. For example, depending upon their use, SDB products may be placed in one of several inventory designations (e.g., "New", "Used", "Loaner", etc.). However, generic billing systems usually cannot support more than one inventory location. In addition, generic systems cannot support the automatic generation of SDB-related forms, patient notes, reminders, etc.

Furthermore, these provider systems typically are tied to wired barcode readers that restrict, for example, their ease of use, places of implementation, etc. Although wireless barcode readers are used, for example, in conjunction with commercial shipping operations, their implementation is unknown in the field of dispensing medical products related to SDB. Moreover, conventional wireless barcode reader systems require expensive, bulky, proprietary equipment that interfaces with proprietary wireless transmitters.

Thus, a need has developed in the art to overcome one or more of these and other disadvantages.

SUMMARY OF THE INVENTION

One aspect of the invention relates to an integrated inventory and patient management system that utilizes a commercially-available barcode scanner that wirelessly communicates scanned data to a database for use in an inventory management system for automatically tracking and generating product and patient information for OSA treatment.

In an exemplary embodiment, a system for managing the treatment of patients diagnosed with sleep-disordered breathing and products used in their treatment is provided, which comprises a barcode scanner that scans the products and retrieves identifying information about the products; a product and patient database that stores the retrieved identifying product information and information about patients; and, a software application running on a computer terminal that can access the product and patient database. The product and patient database will be updated at least when said products are received and/or dispensed, and the updates will be shown in the software application.

In another exemplary embodiment, a system for managing the treatment of patients diagnosed with sleep-disordered breathing and products used in their treatment comprises a wireless barcode scanner that scans the products and retrieves identifying information about the products; a product and patient database that stores the retrieved identifying product information and information about patients; a communications network through which the retrieved identifying product information is stored to the product and patient database; and, a software application running on a computer terminal that can access the product and patient database. The product and patient database will be updated at least when the products are received and/or dispensed, and the updates will be shown in said software application.

In still another exemplary embodiment, a system for managing the treatment of patients diagnosed with sleep-disordered breathing and products used in their treatment is provided that comprises a plurality of barcode scanners that scan the products and retrieve identifying information about the products; a product and patient database that stores the retrieved identifying product information and information about patients; and, a software application running on a computer terminal that can access the product and patient database. The product and patient database will be updated at least when the products are received and/or dispensed, and the updates will be shown in said software application.

In an exemplary embodiment, a system for managing the treatment of patients diagnosed with sleep-disordered breathing and products used in their treatment comprises a plurality of barcode scanners that scan the products and retrieve identifying information about the products; a product and patient database that stores the retrieved identifying product information and information about patients; a first application running on a computer terminal that can access the product and patient database; and, a second application running on a remote device that can access the product and patient database. The product and patient database will be updated at least when the products are received and/or dispensed, and the updates will be shown in the first application and the second application.

In certain exemplary embodiments, a method for managing the treatment of patients diagnosed with sleep-disordered breathing and products used in their treatment comprises scanning barcodes associated with the products to retrieve identifying information about the products; storing the retrieved identifying product information and information about patients in a product and patient database; using a software application running on a computer terminal to access the product and patient database; and, updating the product and patient database at least when the products are received and/or dispensed, wherein the updates may be shown in the software application.

In certain other exemplary embodiments, a method of managing the treatment of patients diagnosed with sleep-disordered breathing and products used in their treatment comprises scanning the products and retrieving identifying information about the products; communicating the retrieved identifying product information over a communications network; storing the retrieved identifying product information and information about patients to a product and patient database; using a software application running on a computer terminal to access the product and patient database; updating the product and patient database being at least when the products are received and/or dispensed; and, showing the updates in said software application.

Certain exemplary embodiments provide a method of dispensing products to be used in the treatment of sleep-disordered breathing, with that method comprising diagnosing a patient; prescribing at least one product to be used by the patient; issuing to the patient at least a barcode indicating the at least one product; and, scanning the at least one barcode at a place where the products may be dispensed.

In yet another embodiment, there is provided packaging for a medical product, comprising an enclosure for a medical product; and a barcode provided to or otherwise associated with the medical product, the barcode being unique to the medical product. The enclosure may be a plastic bag and the barcode may be provided to a product card provided within the plastic bag.

In still another embodiment of the invention, there is provided a method of tracking delivery of a medical product, comprising placing the medical product within a plastic bag which is optionally sealed; providing a product card within the plastic bag, the product card including a barcode that is uniquely associated with the medical product; delivering the medical product to a patient; upon delivery, removing the card from the bag; and returning the card to a provider for processing.

In an embodiment of the invention, there is provided a method of integrating a barcoded inventory system with a billing system, with the method comprising receiving at least one product into inventory by scanning at least one barcode associated with the at least one product; updating a database with information scanned in said receiving step; printing a receipt of products in inventory, said receipt including at least one human-readable serial number and at least one barcode associated with the at least one human-readable identifying serial number; and, scanning into the billing system the at least one barcode from the receipt.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF EMBODIMENTS

Figure 1:
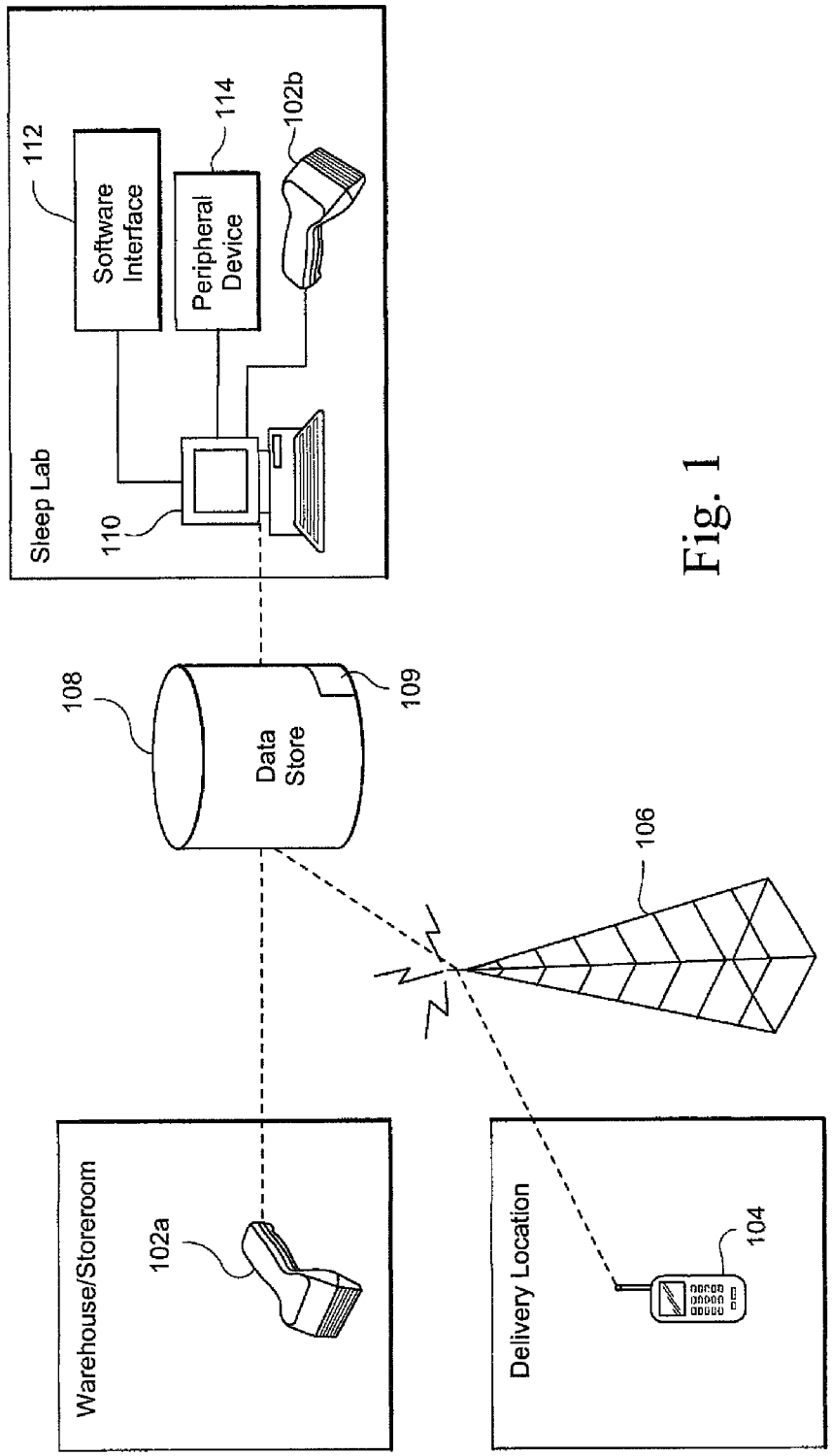
FIG. 1 is a partial schematic view of a system for managing inventory and patient information that uses a plurality of barcode scanners at a plurality of locations.

Referring now to the figures, FIG. 1 is a partial schematic view of a system for managing inventory and patient information that uses a plurality of barcode scanners at a plurality of locations. FIG. 1 is provided as an overview of the components comprising certain exemplary systems. The components comprising various embodiments contemplated herein are described in detail below. Briefly, a first scanner 102a may be located in a warehouse or storeroom. It will be appreciated that such a warehouse may be a provider's warehouse or storage room, a temporary warehouse used during a delivery process, etc.

Figure 2:
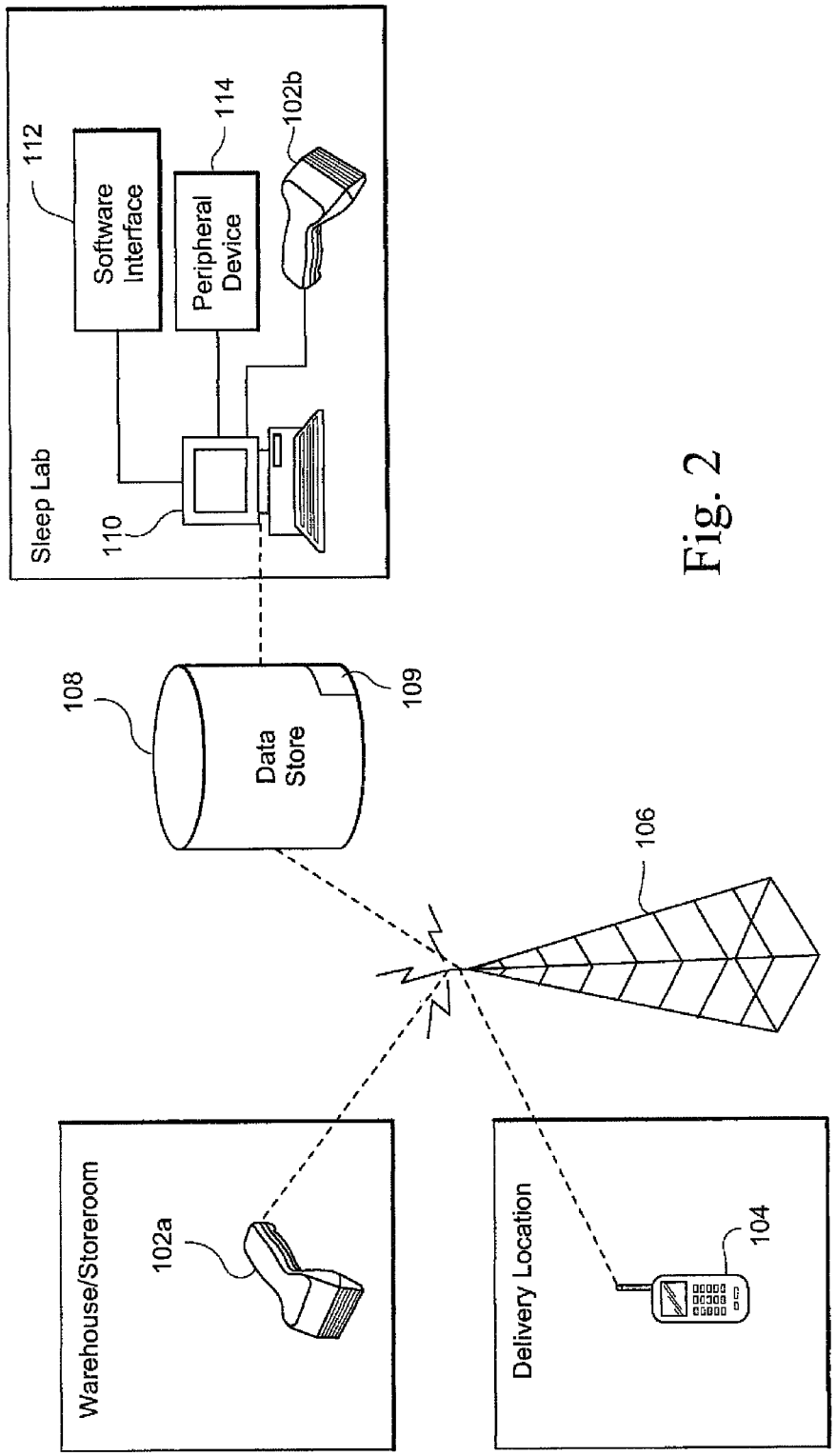
FIG. 2 is a partial schematic view of another system for managing inventory and patient information that uses a plurality of barcode scanners at a plurality of locations.

Scanner 102a preferably is connected to data store 108, which is updated after wireless scanner 102a scans a product. In certain example embodiments, providers and/or sleep labs may not keep inventory on-hand. Thus, when a warehouse/storeroom is managed by a third-party supplier, etc., other configurations may be preferable. For example, as shown in FIG. 2, scanner 102a may be connected to data store (or database) 108 wirelessly. Thus, scanner 102a may communicate with data store 108 through mobile network 106. It will be appreciated that any communications network capable of transmitting scanned-in data may be used, including, for example, the Internet, a LAN, WAN, or the like.

Returning to FIG. 1, wireless scanner/phone 104 similarly is connected to data store 108 through mobile network 106. Within a provider, a computer terminal 110 running a software interface 112 with peripheral/mobile device 114 in communication therewith also can access data store 108. Computer terminal 110 may cause data store 108 to be updated, for example, after a product is scanned by scanner 102b (e.g. when a product is dispensed, returned, etc.), or after a change or changes are made via software interface 112 (e.g. updating client records, adding notes, etc.).

1. Components Comprising Example System for Inventory and Patient Management

The following example embodiments will be described with reference to FIG. 1. A detailed discussion of the major components shown in FIG. 1 and other components follows below.

1.1 Barcode Data and Scanners

Preferably, all products (and/or packaging thereof) received and dispensed by a provider will be tagged with part and serial (or lot) number barcodes. Many barcode formats are available, and these formats vary based on, for example, the width and/or height of the bars, character set, method of encoding, checksum specifications, how much and what kind of data can be held, etc. Proprietary barcode formats are disadvantageous because they typically require additional software and/or hardware resources associated with decoding proprietary formats.

Thus, in certain preferred embodiments, a standardized, commercially available barcode is used to convey information. Some example embodiments may use formats such as, for example, UPC, ISSN, EAN, etc. These formats also are advantageous over proprietary barcode formats, for example, because they generally allow for quick scanning with little or no processing required before storing the scanned information, easy integration with existing commercial products, etc. A barcode preferably will uniquely identify a given product, and also include other product identifying information such as, for example, product identifying information, a serial number, a lot number, etc.

Barcode scanner 102a in FIG. 1 preferably is connected to data store 108, and it certain embodiments, a barcode scanner 102a may be located on the premises of the provider. However, it may not always be possible to establish a physical connection between barcode scanner 102a and data store 108. Accordingly, in some example embodiments, barcode scanner 102a may temporarily store the information it scans in a memory, on a removable storage medium, or the like. That data later may be transferred to data store 108, for example, by copying the data from disk, using a cable link (e.g. serial, parallel, USB, or the like), uploading the data through a network connection, etc. These embodiments have the advantage of being able to use well-established commercial scanners, but require the additional step of transferring data, often manually, and thereby sometimes increasing the time between when an item is scanned and when data store 108 is updated.

The processing of the data scanned by barcode scanner 102a may be necessary before storing it to data store 108, for example, to decode it, format it correctly, perform error checking, etc. In some example embodiments, barcode scanner 102a and/or data store 108 may appropriately manipulate the data before storing it, either alone or in combination. In other example embodiments, a separate processor (not shown) may manipulate the raw data. In certain example embodiments, a separate SQL processor 109 may perform some or all of the required processing. One non-limiting example of when error checking that might be performed occurs after a user inadvertently scans a part number barcode when that user meant to scan a serial number barcode.

Certain example embodiments may include a wireless barcode scanner 104 in place of, or in addition to, barcode scanner 102a. A wireless barcode scanner has advantages relating to, for example, freedom of movement of the person scanning. Wireless barcode scanners also potentially allow data store 108 to be updated without further human action. In certain example embodiments, a data store may be updated as items are scanned, while other example embodiments may update a data store in batches. A wireless barcode scanner may communicate with data store 108 through a wireless communications network 106. Wireless communications network 106 may be any type of wireless network such as, for example, a cell phone network, a Bluetooth network, or the like. It will be appreciated that wireless barcode scanners may be located in warehouses/storerooms, with delivery personnel, or at providers.

Some barcode scanners are particularly well-suited to scanning information and wirelessly conveying that information to another location. Many wireless barcode scanners, however, use expensive, proprietary satellite-based systems. However, several cell phone providers recently have developed cell phone/scanner hybrid technology, for example, using existing cell phone data connections to transmit scanned-in data. One example of such a hybrid is a Motorola cell phone equipped with a Symbol PSM20i bar code scanner, which operates over the Nextel/Sprint wireless network.

Using hybrid cell phone/barcode scanners captures data, but frequently requires data manipulation before the scanned data can be stored to the data store. Thus, in some example embodiments, a processor appropriately manipulates the scanned data before it is stored to data store 108. One commercially available processor that works particularly well with the Nextel/Sprint network is Comet Tracker, developed by ActSoft. It will be appreciated that a processor may manipulate the data before and/or after it is transferred through the wireless communications network.

In certain preferred example embodiments, all error checking and/or manipulations is performed via software running on a terminal rather than requiring an outside processor. According to these embodiments, the Nextel/Sprint processor simply receives data from the network and stores it locally. Additionally, in certain example embodiments, there may not be a need for a separate, on-site SQL server database. According to these embodiments, software running on a terminal automatically may download data from the a web server connected to the telephone/data network.

2.2 Inventory and Patient Database

In certain example embodiments, a single backend database comprising both inventory and patient data is maintained. Preferably, this database may be accessible by a single operator, or multiple operators simultaneously. Multiple-operator accessibility may be advantageous, for example, in embodiments where a scanner or a plurality of scanners are used for inventory purposes, and/or a scanner or a plurality of scanners are used for patient disbursements at a provider. It will be appreciated that in embodiments where multiple-operator accessibility is enabled, careful locking of data may be maintained, for example, to prevent data from being overwritten, report accurate supply information, etc. The database may be accessible in stand-alone and/or networked environments, such as, for example, via software running on a personal computer, via a web interface, through an ODBC connection, over a LAN or WAN, or the like. Certain preferred example embodiments implement a Microsoft Access database that can be queried by SQL statements.

1.2.1 Example Database Design Architecture

Figure 3:
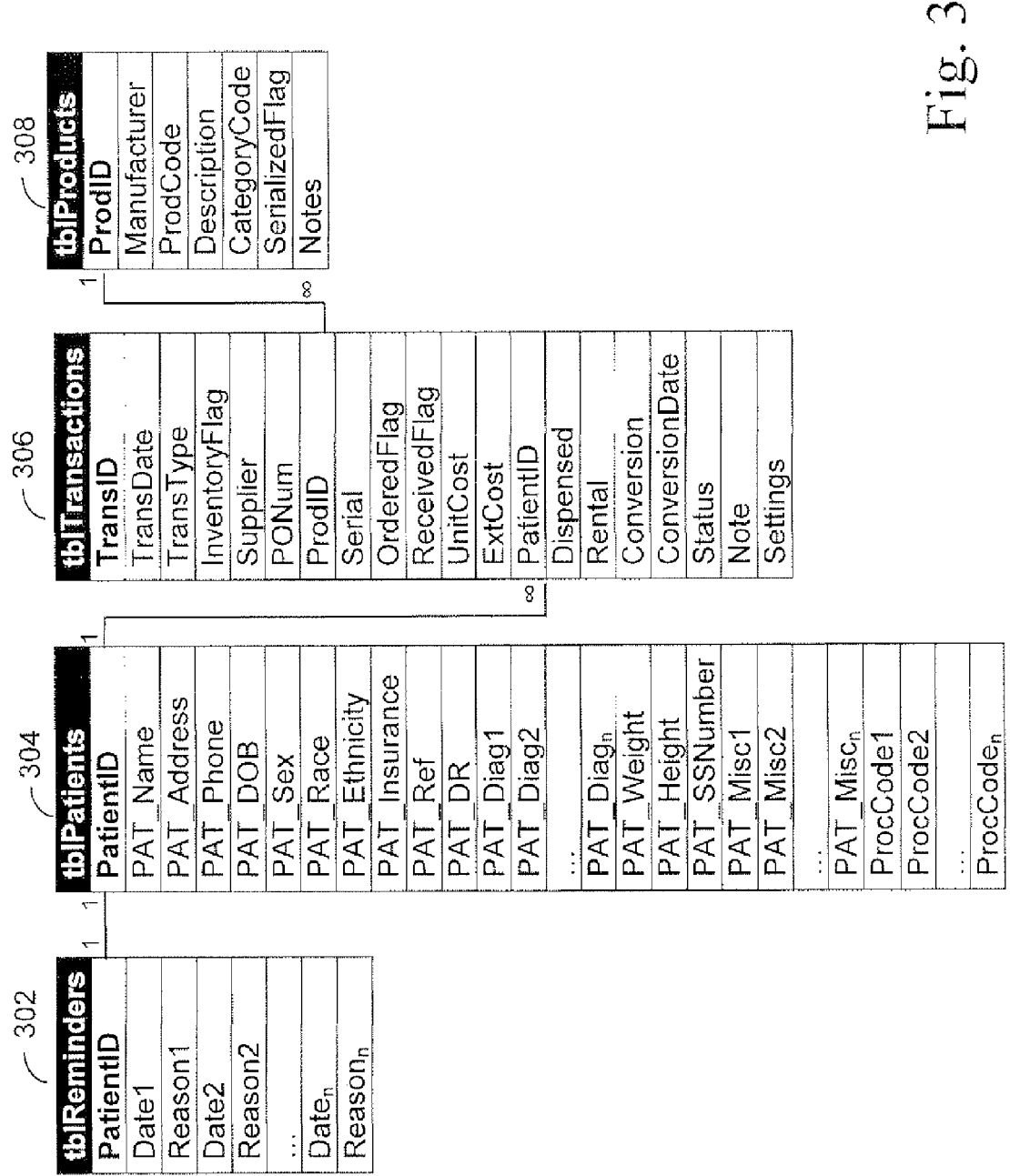
FIG. 3 is an illustrative database schema including exemplary fields for use with a system for managing inventory and patient information in accordance with one exemplary embodiment.

FIG. 3 is an illustrative database schema including exemplary fields for use with a system for managing inventory and patient information in accordance with one exemplary embodiment. It will be appreciated that although the tables, fields, linkages, keys, etc. included in FIG. 3 are appropriate for one example embodiment, the invention is not so limited. For example, tables and/or fields may be used together with, or in place of, those given in FIG. 3, and it will be appreciated that multiple connected databases may be used in place of the single database described below. In FIG. 3, "key" fields (e.g. fields that uniquely identify a record and typically, but no always, link tables together) are given in bold. Although FIG. 3 includes key fields in tables, it will be appreciated that in certain example embodiments other fields may serve as keys in place of, or in addition to, those identified. It also will be appreciated that in certain example embodiments, keys need not be maintained at all. Exemplary symbolic linkages between fields in different tables are show by lines.

While the database in one preferred example embodiment is designed to work with Microsoft Access on a Windows-based computer, the invention is not so limited. On the contrary, other database formats, operating systems, computing platforms, and the like may be substituted as called for in the specific embodiment, with certain preferred embodiments comprising database that can be queried by SQL statements. Other example embodiments could comprise, for example, a MySQL database running on a Linux platform.

1.2.2 Inventory Data

In FIG. 3, inventory data is comprised of transactions table 306 and products table 308. Preferably, transactions table 306 and products table 308 are linked via a product identification code (ProdID), which preferably is a key field in products table 308. Many transactions may be associated with each product. For example, a particular product may be ordered, received into inventory, rented to a patient, returned by a patient, rented to another patient, etc.

The first field listed in transactions table 306 is TransID, which preferably is a unique identifier associated with each transaction. TransDate records the data of the transaction, and TransType indicates the type of transaction. For example, transaction type may be, for example, "order sent," "shipment received," "device loaned," "device returned," etc.

Several fields may keep track of product-specific data. InventoryFlag preferably indicates whether a device currently is in inventory, and Supplier specifies the party (or parties) from whom the device may be available. PONum preferably is a unique product order number. Any serial or lot number present on the product may be stored in the Serial field. Respectively, OrderedFlag and ReceivedFlag indicate whether a given product was ordered and/or received. By monitoring these fields, it is possible, for example, to track order status from suppliers. UnitCost and ExtCost respectively may indicate the price the supplier charges per product unit, and any other extra costs associated therewith.

Other fields may reflect the relationship between patient and product. Flags may indicate whether, for example, the product was dispensed (DispensedFlag), the product is a rental unit (RentalFlag), whether the unit was converted (e.g. from a rental unit to a loaner unit), etc. Dates may be associated with these flags (e.g. ConversionDate).

It will be appreciated that a permanent record of all transactions may be kept, for example, to establish an audit trail, research how much and which type of equipment is being dispensed over a given period, chart patient disbursements, etc. It also will be appreciated that such records preferably will be kept confidential and otherwise maintained in accordance with applicable law.

Other data may be stored in transactions table 306, including, for example, the status of the transaction (Status) (e.g. pending approval, waiting customer pick-up, etc.), other notes (Notes), and custom settings information (Settings). Preferably, a unique identifier for patients (PatientID, described in further detail below) may be used to link many transactions to individual patients.

Products table 308 preferably is comprised of data relating to a specific product. It may include manufacturer information (Manufacturer); a product code (ProdCode) describing, for example, the type of product, model number, etc.; a description of the product (Description); a category into which the product fits, for example, CPAP device, flow generator, etc.; and the like. Preferably, products table 308 also will indicate whether a particular product has a serial number associated therewith (SerializedFlag). Additional notes also may be stored (Notes).

1.2.3 Patient Data

In FIG. 3, patient data is comprised of reminders table 302 and patients table 304. Preferably, reminders table 302 and patients table 304 are linked via a patient id code (PatientID), which preferably is a key field in both tables. Each patient preferably is associated with one record in reminders table 302 and potentially multiple records in transactions database 306.

The first field listed in reminders table 302 is PatientID, which is preferably a unique identifier associated with each patient. Reminders table 302 preferably contains a plurality of date fields and respective reason fields. Thus, a reminder may be set (e.g. by an operator or automatically by the system) for a certain date ($Date_i$), and the reason that reminder was set also will be stored in an associated field ($Reason_i$). In a preferred example embodiment, at least five date/reason pairings will be stored in reminders table 302 for each patient. Also in a preferred embodiment, at least one date/reason pairing will be reserved for a compliance check-up, and at least one date/reason pairing will be reserved for a supplies check-up. In certain example embodiments, reminders may be generated automatically. For example, a reminder may be created automatically reminding a patient to schedule a follow-up visit in a certain number of weeks, etc. Other non-limiting examples include reminding a respiratory therapist to follow-up with a patient regarding compliance; reminding a customer service representative to follow-up with a patient regarding supplies replacement; reminding persons to follow-up with equipment inspection.

Patients table 304 preferably includes personal and demographic information about each patient such as, for example, patient name (PAT_Name); address (PAT_Address); phone number (PAT_Phone); date of birth (PAT_DOB); gender (PAT_Sex); race (PAT_Race); ethnicity (PAT_Ethnicity); weight (PAT_Weight); height (PAT_Height); social security number (PAT_SSNumber); etc. Other information such as, for example, insurance information (PAT_Insurance), referral source (PAT_Ref), primary-care physician (PAT_DR), etc. also may be maintained.

Information as to the patient's diagnosed medical conditions ($PAT\_Diag_1 \ldots PAT\_Diag_n$), history of medical procedures ($ProcCode_1 \ldots ProcCode_n$), and other miscellaneous data ($PAT\_Misc_1 \ldots PAT\_Misc_n$) may be maintained. This information may be critical, for example, to monitoring a patient's progress, responses to treatments, etc. This data preferably will be updated and supplemented at least as long as the patient is seeking treatment through the provider. In some example embodiments, records may be transferable to other providers. It will be appreciated that such records preferably will be kept confidential and otherwise maintained in accordance with applicable law.

3.3 Management Software

Software interface 208 is provided for interfacing with data store 204. Software interface 208 preferably is accessible by computer terminal 206. In certain example embodiments, a plurality of software interfaces 208 may run on a plurality of computer terminals 206, to allow, for example, multiple-user access to data store 204. It will be appreciated that software interface 208, or a variant thereof, may be accessible via other devices such as, for example, a PDA, etc. It also will be appreciated that the software interface may function as a front-end application, a back-end application, in a client-server relationship, etc., depending on the particular embodiment implemented.

The following sections categorize and describe some of the main features accessible in one preferred example embodiment. It will be appreciated, however, that the list of features given below and the classifications of those features are for non-limiting, illustrative purposes only. The following categories will be described with reference to FIG. 4, which is an illustrative menu of non-limiting options available for use with a system for managing inventory and patient information in accordance with one example embodiment. From the software interface screen S402, it is possible to access patient information (S404), transactions (S406), reports (S408), and administrative functions (S410).

1.3.1 Patient Information

Patients screen S404 allows operators to access Patient Data screen S412, Notes screen S414, and Reminders screen S416. Patient Data screen S412 allows operators to view and/or edit existing information about patients, add new patients to the database, delete existing patients, etc. In some example embodiments, patients may enter their own data.

Notes screen S414 allows operators to create new and view or delete existing patient notes. Notes also may be generated automatically by the system. Similarly, Reminders screen S416 allows operators to create new and view or delete existing patient reminders. Reminders also may be generated automatically by the system reminding, for example, the patient of subsequent appointments, the treating physician to check the patient's progress, etc.

1.3.2 Transaction Tracking

Many of the options in Transactions screen S406 integrate well with a barcode scanner. In CMN screen S418, operators can create certifications of medical need and generate letters of medical necessity in LMN screen S426. Operators can scan a particular product to auto-populate fields on a standardized forms and/or letters, indicating, for example, the exact type of equipment the patient is being needs.

Patients returning products do not necessarily have to fill out extensive paperwork, nor do provider employees have to manually update inventories, as operators can scan returned devices in Patient Return screen S420 and issue manufacturer's authorizations through RMA screen S428. Similarly, patients receiving products may receive usage instructions, terms and agreements, bills, receipts, etc. generated when an operator dispenses a product using Patient Dispensing screen S430, and information about the product(s) a patient receives also may be stored.

Expected inventory counts can be updated automatically when a unit or units are ordered using Create Purchase Order screen S422 (and/or using Supplemental Order Form screen S432), and inventory-on-hand counts and details can be updated automatically when orders arrive after they are scanned using receive shipment from Supplier screen S424. Similarly, appropriate flags can be changed in the database after a rental is converted and scanned in View/Convert Rentals screen S436.

Operators also may schedule patient follow-ups using Patient Follow-up screen S434.

1.3.3 Reports Generation

Reports screen S408 controls the generation of reports. Many reports preferably may be customized, for example, by applying various filters, restricting date ranges, searching for specific products only, etc. Preferably, the output of these reports also may be integrated into other data analysis software. Various patient reports are available through Patient Queries screen S442, and reminder reports are available through Reminders screen S452.

Dispensing screen S438 displays information such as, for example, who has received products, which products have been dispensed, when the products were dispensed, etc. Open Loaners screen S446 and Open Rentals screen S448 respectively report on the number of loaner and rental products issued to patients. Whereas Dispensing screen S438 displays information about issued (or previously issued) products, Inventory screen S440 preferably reports on all inventory—e.g. products issued, not issued, ordered, etc.

Patient Returns screen S456 preferably tracks all patient returns of products including, for example, when patients require a different product, require a product upgrade, are non-compliant or have completed treatment, etc. It is important to note that returned products can be easily placed and tracked via one or more return-associated inventories, e.g., "Used", "Loaner", "Donated", etc.

RMAs screen S460 shows how many products have been returned for, for example, defects, etc.

Information about ordered products preferably is also available through Purchase Orders screen S444, which may show the existence and status of purchase orders. Preferably, Receiving screen S450 is tied into the inventory to report when new shipments are received and processed. Ordered v. Received screen S454 juxtaposes outstanding orders with received orders.

Reorders screen S458 allows users to easily determine which products have fallen below a user-defined minimum level and need to be re-ordered. This report preferably is generated on an exception-basis.

Figure 4:
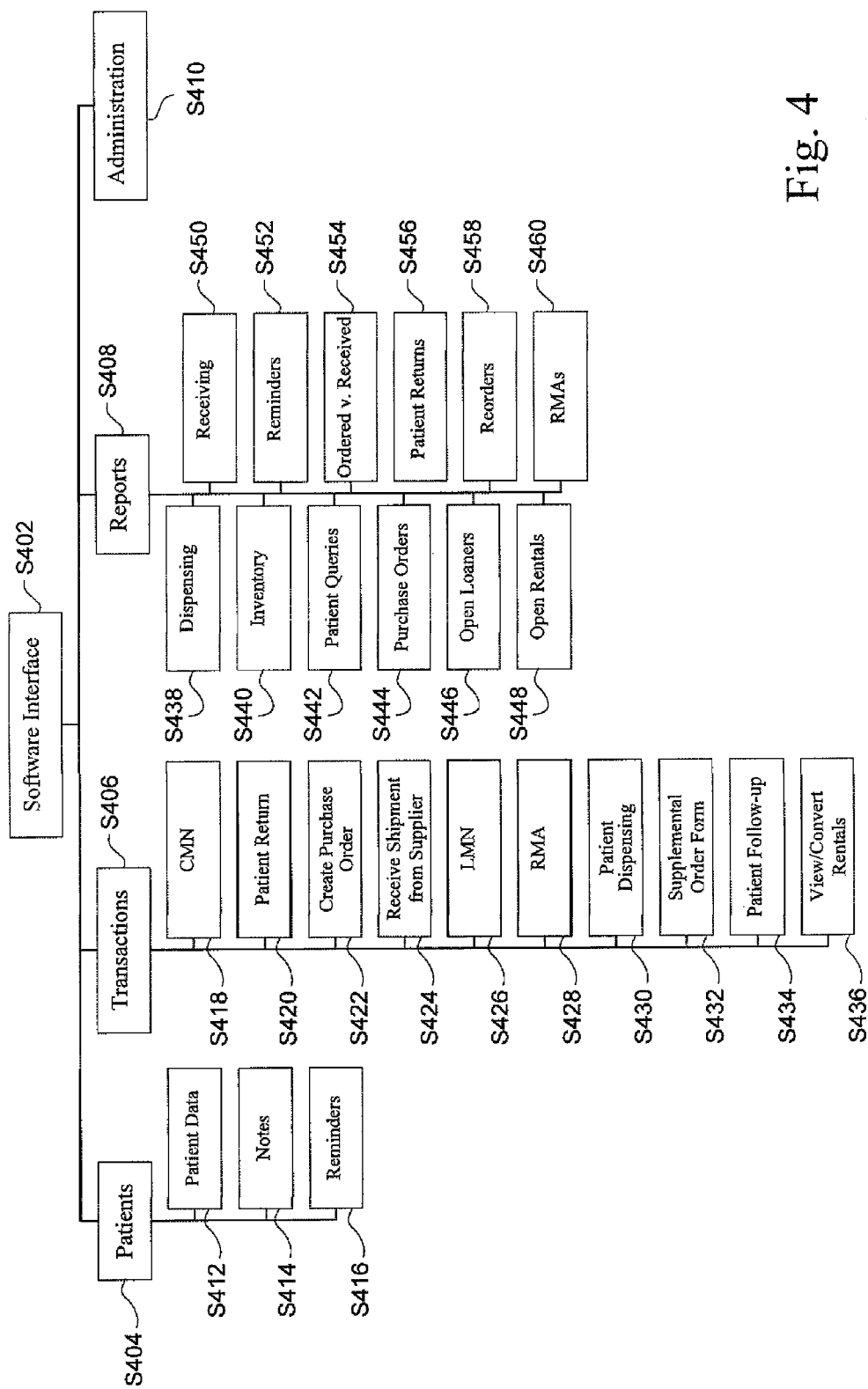
FIG. 4 is an illustrative menu of non-limiting options available for use with a system for managing inventory and patient information in accordance with one example embodiment.

Other reports are possible but are not shown in FIG. 4, such as, for example, histories of products, patients, etc. It will be appreciated that the foregoing reports and the contents described in connection therewith are for illustrative, non-limiting purposes only. On the contrary, many other reports with various content may be presented.

1.3.4 Administrative Functions

Various administrative functions may be available through Administration screen S410. For example, authorized users may add or change logon rights for operators, set or reset passwords, etc. More detailed administrative functions also may be allowed. For example, operators may, through this feature, change the contents of certain menu options, printable forms, bills, etc.

2. Example Implementations

Figure 5A:
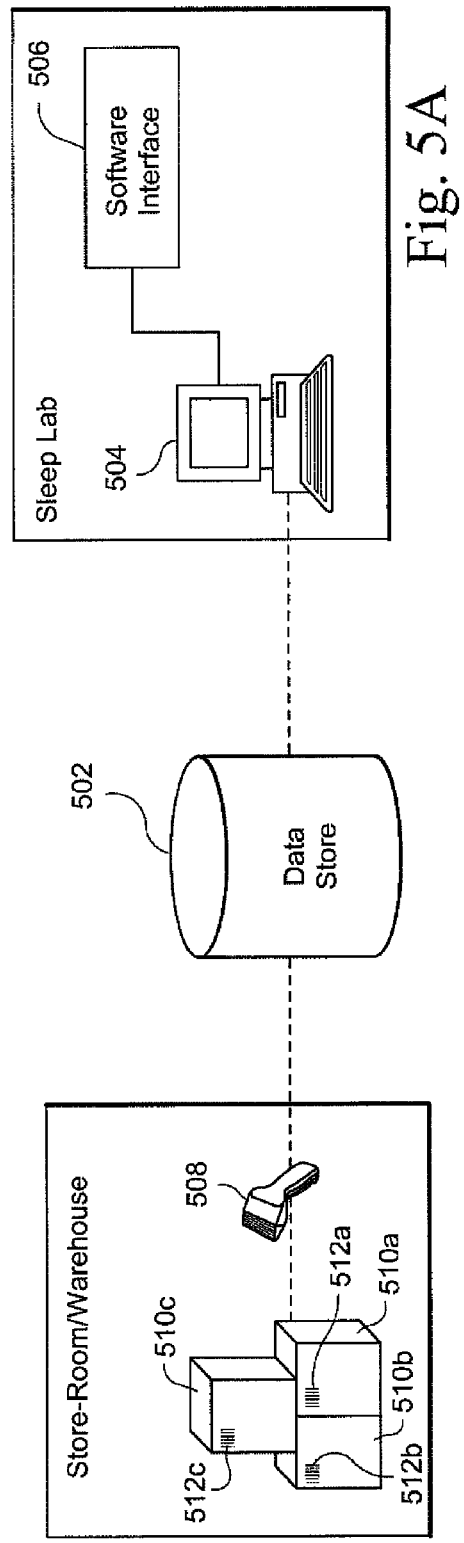
FIG. 5A is a partial schematic view of a system for managing inventory and patient information that uses a barcode scanner in a storeroom and/or warehouse in accordance with one example embodiment.
Figure 5B:
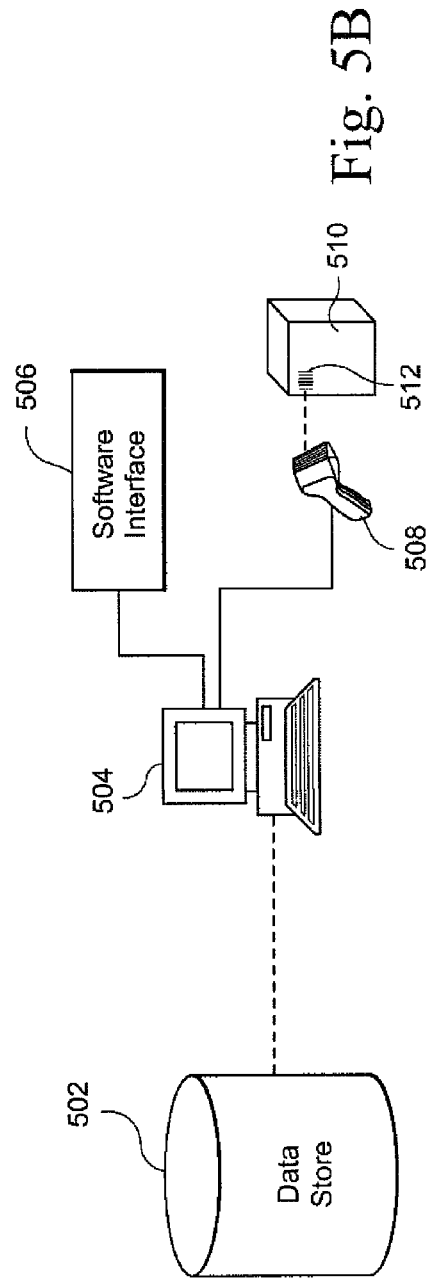
FIG. 5B is a partial schematic view of a system for managing inventory and patient information that uses a barcode scanner in the front-office and/or fitting room at a provider in accordance with one example embodiment.
Figure 5C:
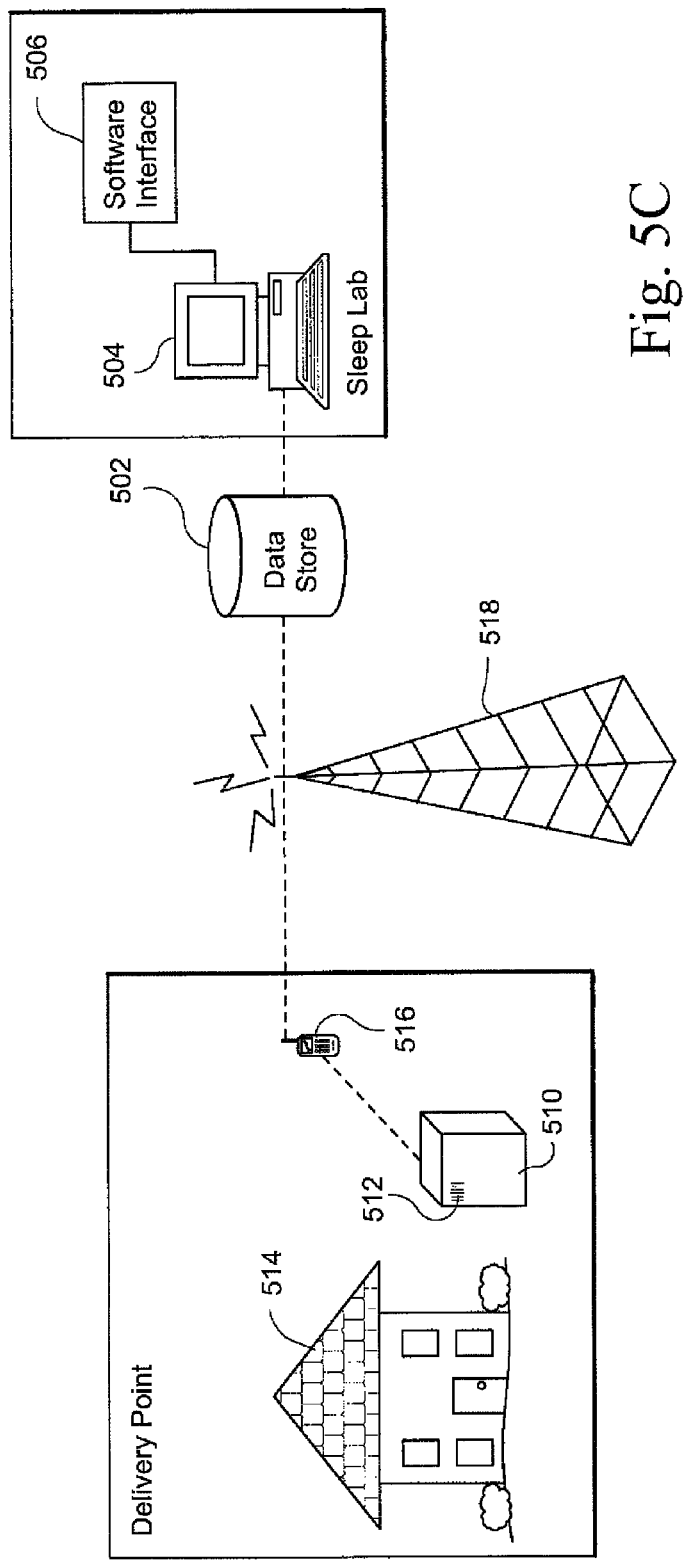
FIG. 5C is a partial schematic view of a system for managing inventory and patient information that uses a barcode scanner at a point of delivery in accordance with one example embodiment.

Embodiments of the above-described example systems can be adapted and modified to meet the specific needs of providers, patients, etc. The following three example embodiments, described with reference to FIGS. 5A, 5B, and 5C, show that the system described in FIG. 1 can be implemented to provide inventory and patient management systems with scanners in storerooms and/or warehouses, in a provider's front-office and/or fitting room, and at points of delivery. It will be appreciated that other modifications are possible and that the following example implementations are for illustrative, non-limiting purposes only.

Several system components are common to FIGS. 5A, 5B, and 5C. A data store 502 comprising patient and inventory information is accessible by a computer terminal 504. Software interface 506 runs on computer terminal 504, and enables its operators, for example, to view inventory in stock and/or on order, track and/or record disbursements, etc. Other system components will be described with relation to specific example embodiments below.

1.1 Store-Room/Warehouse Maintenance

FIG. 5A is a partial schematic view of a system for managing inventory and patient information that uses a barcode scanner in a storeroom and/or warehouse in accordance with one example embodiment. Providers that dispense products preferably will track the inventory they have on-hand, for example, to monitor when they are running low on a product and should place an order for that product, to audit the quantity and types of products dispensed (and not dispensed), etc. Thus, a barcode scanner 508 preferably is located in the storeroom and/or warehouse of the provider, for example, to track incoming shipments and outgoing disbursements. Preferably products 510a-c will be tagged, respectively, with barcodes 512a-c, all readable by barcode scanner 508. The information scanned by barcode scanner 508 (preferably including, for example, identifying product information, serial numbers, lot numbers, etc.) is sent to data store 502. Software interface 506 running on computer terminal 504 connected to data store 502 is changed during and/or after this update to data store 502 to indicate, for example, the changes in inventory. Software interface 506 also may, for example, automatically generate order forms, communicating with the storeroom and/or warehouse and/or supplier, etc.

It will be appreciated that while this example embodiment has been described in relation to the storeroom and/or warehouse at a provider, the present invention is not so limited. For example, this example embodiment also may be useful in a manufaturer or distributor's warehouses and/or storerooms. Manufacturers and/or distributors could use such a system, for example, to track how many and what type of product they are sending to providers (and/or patients directly) to better manage their production cycles, anticipate orders, etc. Certain modifications may be made to this system, including, for example, those described with respect to FIG. 2. Thus, in situations where a warehouse and provider are separate, it may be advantageous, for example, to use a barcode scanner connected to a data store through a mobile network.

2.2 Provider Operations

FIG. 5B is a partial schematic view of a system for managing inventory and patient information that uses a barcode scanner in the front-office and/or fitting room at a provider in accordance with one example embodiment. Providers can, for example, track disbursements of products, accept product returns, convert rental units to owned units, monitor patients' diagnoses and compliance, associate patients with the products they are given, etc. In this example embodiment, data store 502 is accessible by software interface 506 through computer terminal 504. Scanner 508 preferably is connected to computer terminal 504 to scan barcode 512 on product 510 and transmit the information to data store 502. In other example embodiments, such as embodiments where scanner barcode 508 is not connected to computer terminal 504, information scanned by barcode scanner 508 may be stored to data store 502 without using computer terminal 504. Data store 502 is changed during and/or after the scan to indicate, for example, the changes in inventory.

3.3 Delivery of Products to Patients

FIG. 5C is a partial schematic view of a system for managing inventory and patient information that uses a barcode scanner at a point of delivery in accordance with one example embodiment. When a patient is diagnosed with SDB, due for new and/or replacement equipment, etc., providers may deliver products directly to that patient. In some example embodiments, orders will be processed automatically after a diagnosis is entered through software interface 506.

A product 510 with a barcode 512 associated therewith is delivered. Delivery point 514 may be, for example, a patient's home, place of work, etc. When the product is delivered to delivery point 514, barcode 512 preferably is scanned by wireless barcode scanner 516. The data scanned by wireless barcode scanner 516 then is sent through wireless communications network 518 and stored in data store 502. Software interface 506 running on computer terminal 504 connected to data store 502 is changed during and/or after this update to data store 502 to indicate, for example, the changes in inventory. Software interface 506 also automatically may generate reminders, notes, and the like.

It will be appreciated that while this example embodiment has been described in relation to disbursements from a provider to a patient, the present invention is not so limited. For example, this example embodiment also may be for delivering products to providers from manufacturers and/or distributors' warehouses and/or storerooms (e.g. when a provider runs low on, or out of, stock, etc.), to a provider's warehouses and/or storerooms from a provider (e.g. when defective, broken, or other products are returned, etc.).

3. Example Method for Inventory and Patient Management

Figure 7:
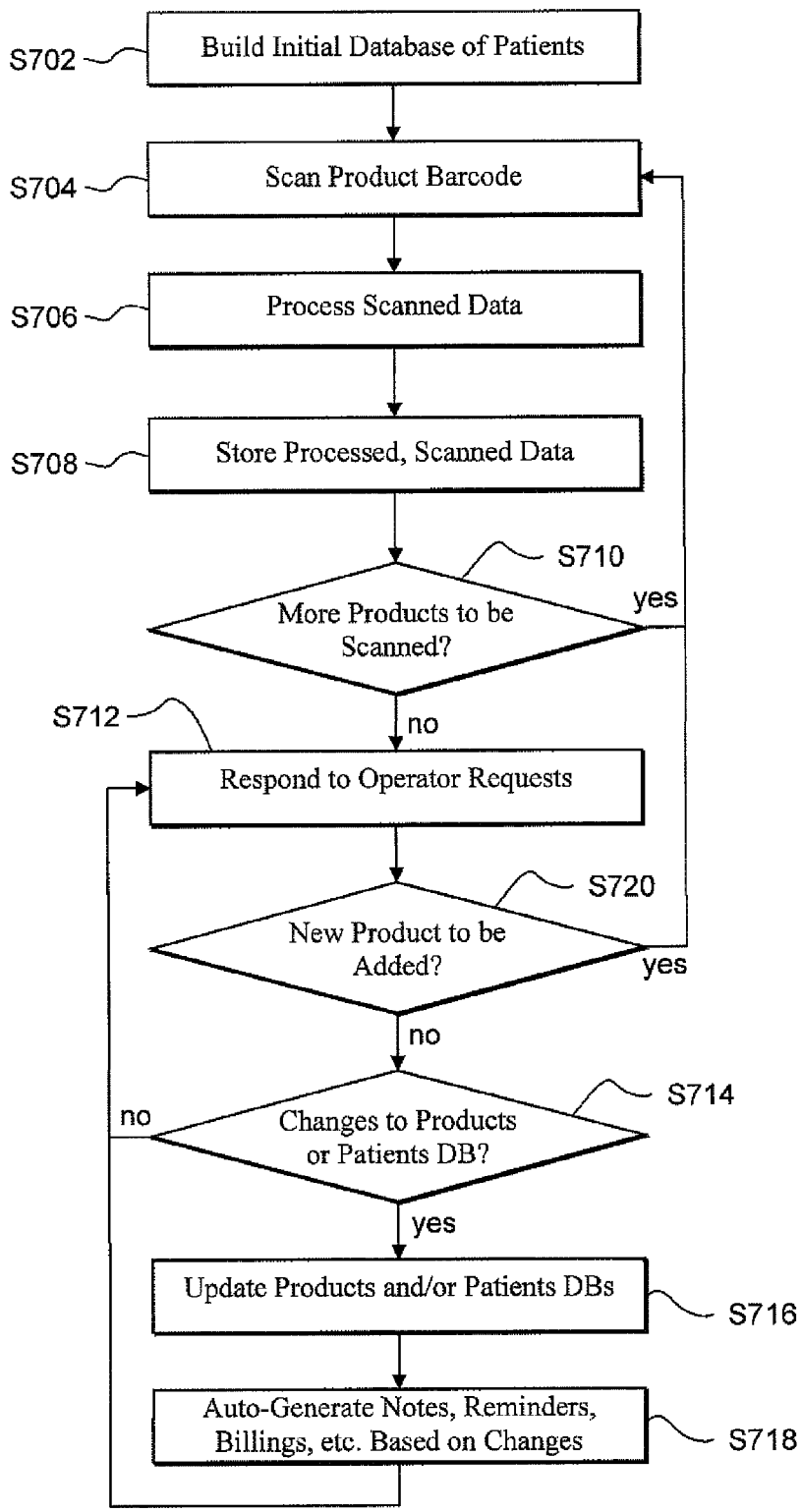
FIG. 7 is a flowchart of an exemplary process for managing inventory and patient information in accordance with one example embodiment.

A database of patients and products in inventory must be built before providers can start dispensing products. The tables and fields comprising patient information is described above with reference to FIG. 3. FIG. 7 is a flowchart of an exemplary process for managing inventory and patient information in accordance with one example embodiment. Preferably, patient information will be entered into the database by, for example, a provider employee, as shown in step S702. The data may be entered, for example, by migrating existing data from another application, manually reentering the data, etc. It will be appreciated that existing patient data may be entered all at once, in batches, as patients visit providers, etc. In steps not shown, it will be appreciated that future patients may be added to the database as they come to the provider.

Step S704 begins the process of building a database of products. Illustrative data comprising product information is described above in detail, with reference to FIG. 3. Preferably, each product will contain a barcode with information encoded therein (e.g. product information, a serial number, a lot number, etc) which can be used to identify a given product.

In step S706, the scanned data is processed, depending on the example embodiment. Processing may be required, for example, to appropriately delimit fields, convert foreign characters, etc. In certain example embodiments, the processing in step S706 also will ensure that the data is error-free—e.g., step S706 may determine that all necessary fields have been appropriately read and parsed, are ready for storage, etc. Error checking may be performed by hardware, software, and/or a combination thereof. For example, error checking may determine whether a product code scanned as expected, or was a serial number scanned by mistake; whether an inventory designated to receive the product; whether the serialized product accidentally scanned twice; etc. In step S708, the processed, scanned data is stored to the database. If there are more products to be scanned, step S710 will return the system to step S704 to continue with the scanning process.

If there are no more products to be scanned, for example, because the initial database is completely built, step S710 will direct the system to wait for an operator request in step S712. Operators may be provider technicians, doctors, etc. A non-limiting list of specific actions operators may take is discussed above in detail with reference to FIG. 4. Briefly, operators may, for example, view patient information, begin a transaction (e.g. rent, lend, and/or return a device, etc.), request a report, change administrative settings of the system, etc. If new products are to be added to the database, step S720 returns the system to step S704, where products may be scanned in the above-described manner.

Step S714 will determine whether such an operation request necessitates a change to product and/or patient information in the database. For example, if a patient is diagnosed with OSA and is issued a CPAP device, the system preferably will update patient information included in the database to reflect that, for example, the patient was examined on a certain date, was diagnosed with a particular condition, etc. In the same example, product information included in the database preferably would be updated to reflect that, for example, a particular CPAP device with a particular serial number furnished by a particular manufacturer was issued as a rental unit at a specific rate. If a change to the database is required as determined by step S714, the system proceeds to step S716.

Other user requests may not necessitate a change to product and/or patient information. For example, if the operator merely queries the system to determine the number of CPAP devices in stock, preferably no changes would be made to the database. If no change to the database is required as determined by step S714, the system returns to step S712 to await further operator requests.

Step S716 updates product and/or patient information in the database, if necessary. Many standardized forms may be generated based on these changes, and some example embodiments will generate forms, notes, reminders, and the like automatically when a change is made. Returning to the example given above, the system may automatically generate a Physician's Certification for CPAP, create a reminder to check on the patient after a certain time has elapsed, print terms and conditions of the rental, etc. Thus, based on the changes made in step S716, step S718 may automatically generate notes, reminders, billing information, and the like, as appropriate. After these steps are completed, the operator may make further requests of the system in step S712.

In steps not shown in FIG. 7, an operator request may require a device to be dispensed to a patient. In such a case, the system preferably scans the barcode of the device using a process analogous to the one described above and updates products and/or patient information accordingly to track the disbursement, generate automatic content, etc. A non-limiting list for when an operator request may require a product to be scanned is given above with reference to FIG. 4.

If a new product or products are to be added to the database (e.g. when inventory drops below a threshold value and replacements arrive, etc.), step S720 directs the system to step S704 to scan the barcode of the new product(s), as described above.

3.1 Example of Menu Driven Notes-Patient Management

Typically, a provider will conduct a follow up interview with the patient at some point after the product has been delivered and or used by the patient, e.g., 24 hours, three months, etc., after delivery/use. The interview will usually take place over the phone, during which time the home care provider will take notes on the patient's responses. Once the interview is concluded, the provider usually manually enters information into a database based on the notes.

According to one aspect of the invention, the software interface may generate notes automatically based on a menu-driven system of common questions and answers. Sample questions may include one or more of the following non-limiting examples:

How many hours are you using your equipment each night?
Are you experiencing any problems with your equipment?
Are you experiencing any problems with your mask?Sample answers may include one or more of the following non-limiting examples: using the equipment for X hours per night; no equipment problems; waking up less; snoring eliminated; etc.

Thus, the "notes" from the telephone interview will be generated during the telephone call, such that there is no need for the provider to separately enter the information after the phone call ends. Instead, the provider can simply hit a "Close and Save" button and the notes will automatically be generated. Sample data from the interview can include text and/or audio and/or video of the patient's responses.

The menu-driven system can be a stand alone system, or it can be built into the software interface described in relation to FIG. 7, e.g., step S718 ("Auto-Generate Notes").

4. Example Ancillary Functionality 4.1 Remote Device Connections

Figure 6B:
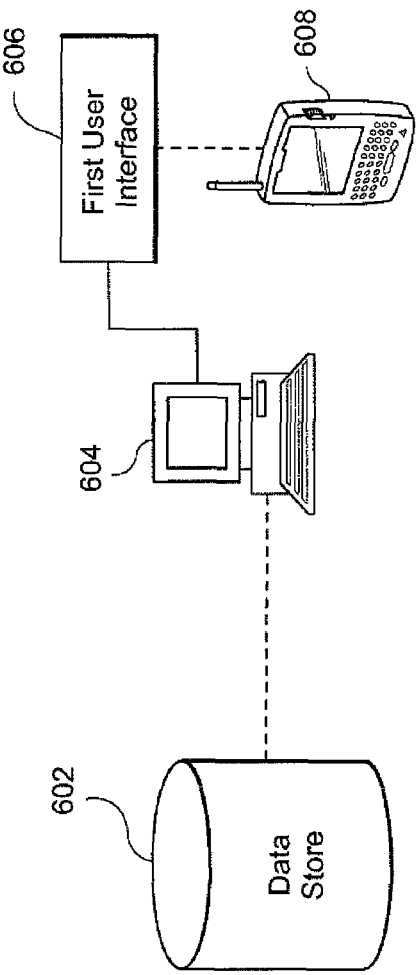
FIG. 6B is a partial schematic view of a system for managing inventory and patient information with a remote device for accessing the system in accordance with another example embodiment.
Figure 6A:
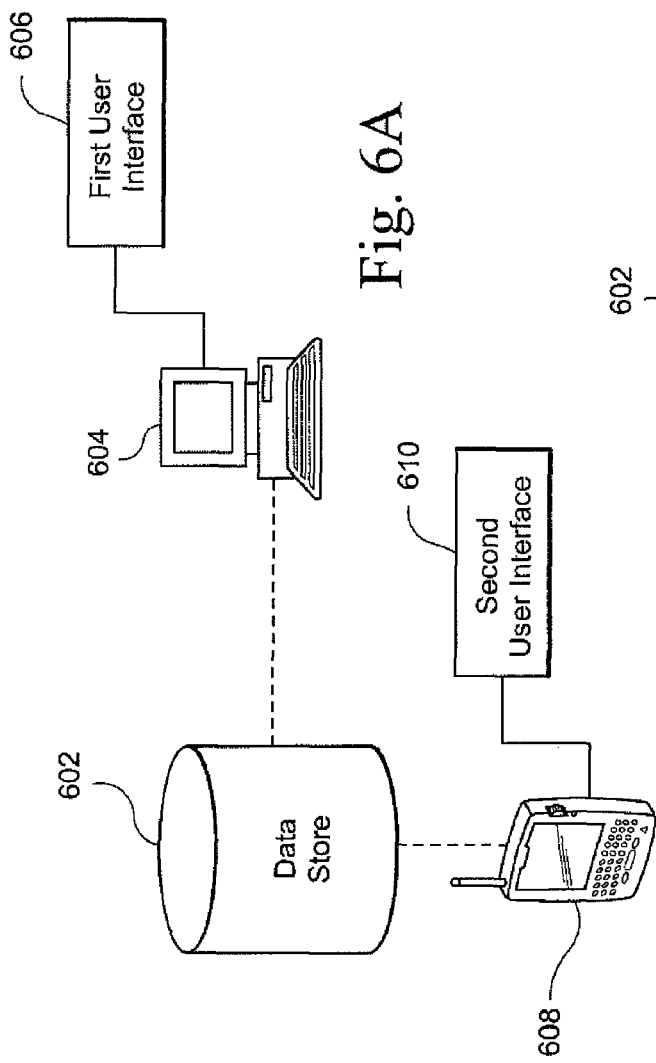
FIG. 6A is a partial schematic view of a system for managing inventory and patient information with a remote device for accessing the system in accordance with one example embodiment.
Figure 6C:
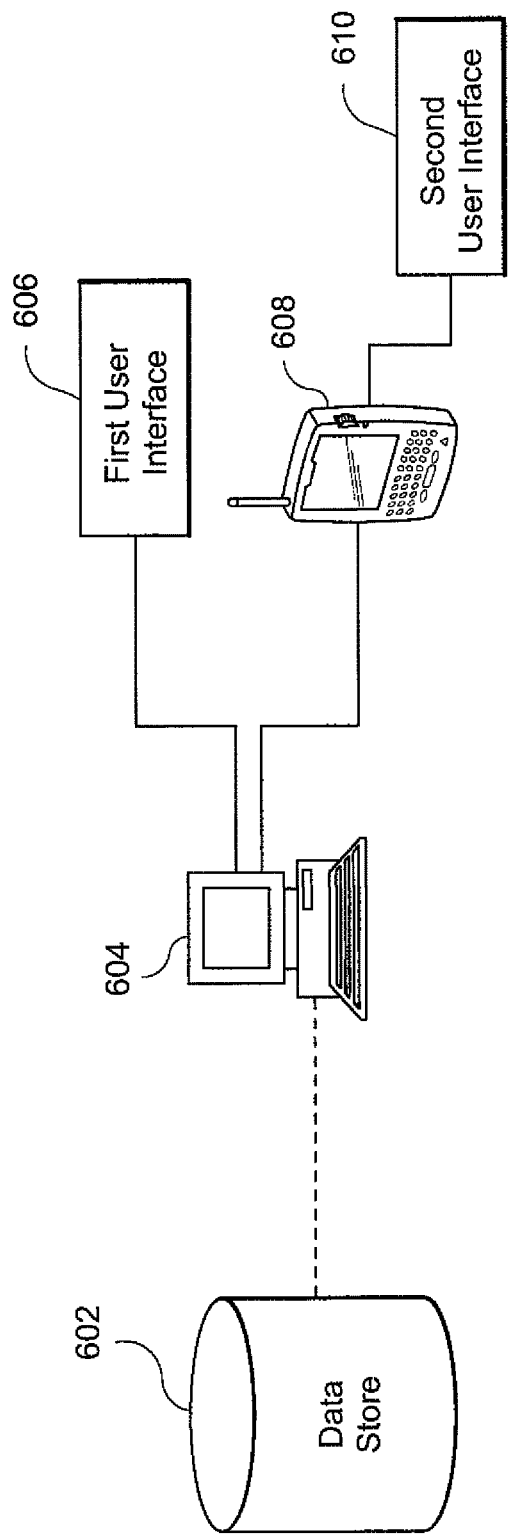
FIG. 6C is a partial schematic view of a system for managing inventory and patient information with a remote device for accessing the system in accordance with yet another example embodiment.

Remote devices may be attached to an above-described example system, as shown in FIGS. 6A, 6B, and 6C. FIGS. 6A, 6B, and 6C are all partial schematic views of systems for managing inventory and patient information with a remote device for accessing the system in accordance with example embodiments. In FIGS. 6A, 6B, and 6C, a data store 602 is connected to a computer terminal 604, which enables a first user interface 606 to access data store 602. Also included in FIGS. 6A, 6B, and 6C, is a mobile device 608. Mobile device may be, for example, a PDA, a laptop, a remote terminal, etc. It will be appreciated that a plurality of remote devices (not shown) may be connected to these systems. It also will be appreciated that, in certain example embodiments, the mobile devices may need to "hot-synched" with a fixed connection (e.g. the terminal) before they can be used remotely and/or before the database(s) are updated.

In FIG. 6A, a mobile device 608 enables a second user interface 610 to access data store 602, independent of computer terminal 604 and first user interface 606. Second user interface 610 may be the same kind of interface as first user interface 606, simply running on mobile device 608. In other embodiments, second user interface 610 may be different from first user interface 606. Preferably, any changes made to data store 602 are reflected both on first user interface 606 and second user interface 608. In some example embodiments, mobile device may communicate with data store 602 through a wireless Internet connection, a cell phone network, etc.

In FIG. 6B, mobile device 608 may use first user interface 606 to access data store 602. In some example embodiments, this arrangement may be disadvantageous if first user interface 606 must communicate through computer terminal 604 to access data store 602, because, for example, it requires computer terminal 604 to be on and accessible. In other example embodiments, mobile device 608 may use first user interface 606, but mobile device 608 may have a connection to data store 602 independent of computer terminal 604. This arrangement is more advantageous, and may be used, for example, when first user interface is implemented as a web page.

FIG. 6C, mobile device 608 has a second user interface 610. However, in this example embodiment, changes made via second user interface 610 must be transmitted through computer terminal 604 before being reflected in data store 602. This arrangement may be disadvantageous because it requires, for example, computer terminal 604 to be on and active. However, this example embodiment may be used in cases where mobile device 608 does not or cannot communicate with data store 602 (e.g. it is not wirelessly enabled, it requires docking before transmitting information, etc.).

4.2 Barcode-Based Prescribing and Order-Filling

Handwritten prescriptions are inherently disadvantageous. For example, they may be hard to read, innocent transposition of numbers and/or letters are possible, etc. Barcoding products may eliminate these and other problems by allowing, for example, physicians to print the barcode of an appropriate product after a diagnosis, and thus allow a supply center to scan the barcode to ensure that the proper product is dispensed.

Figure 8:
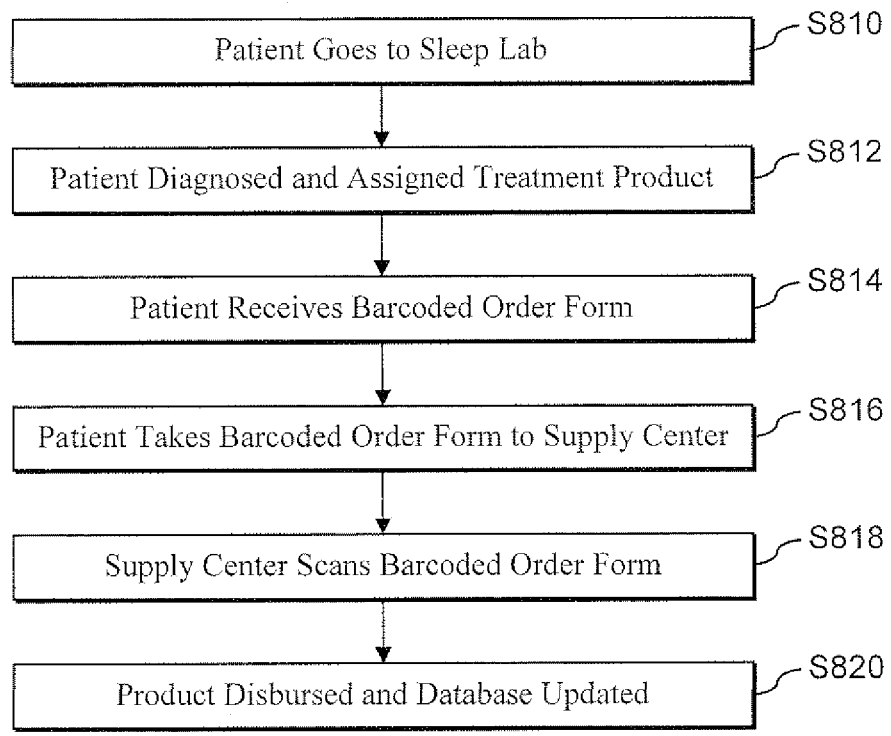
FIG. 8 is a flowchart of an exemplary process for prescribing and dispensing barcoded products.

FIG. 8 is a flowchart of an exemplary process for prescribing and dispensing barcoded products. A patient goes to a physician and/or sleep lab in step S810. In step S812, a patient is diagnosed and assigned a treatment product. Then, in step S814, the patient receives a barcoded order form for the appropriate product. It will be appreciated that the patient may receive the barcoded order form from the physician, sleep lab, via the mail, etc. The patient then takes the barcoded order form to a provider in step S818 to obtain the appropriate product. Preferably, the barcoded order form is scanned in step S818 with little or no additional manual entry required. Finally, in step S820, the product is dispensed and the database is updated appropriately.

4.3 Barcoded Product Cards

In certain example embodiments, barcoded information sheets or cards may be included in product packaging to assist, for example, in dispensing products after diagnoses, return products, inform non-treating physicians of prescribed devices, etc. Currently, when a product delivery is made, a provider representative (e.g., respiratory technician, delivery driver, etc.) will fill out a delivery sheet (e.g., by hand) that includes a description of the product (e.g., quantity, lot number, model). The delivery sheet or invoice will then be returned to the provider whereby additional personnel will process the delivery sheet, e.g., take the information from the delivery sheet and enter it into a database, billing system, etc., for example, for tracking or recordkeeping. Errors can be introduced by either the driver or the additional personnel, e.g., if information is not legible or is simply transposed. Moreover, the entry of this additional information requires additional labor as well.

In one embodiment of the invention, a product which is delivered to a customer or patient is provided with or otherwise associated with a unique bar code. For example, some products, e.g., masks, are typically provided in a plastic bag. A product card or information sheet may also be provided in the bag, e.g., for ResMed products. The card or sheet which is normally provided with a product can additionally be provided with the unique bar code. The card or sheet or a portion thereof (e.g., separable by a perforated portion clearly marked for use by the driver/technician) can be removed by the driver and simply stapled to the delivery sheet or invoice. Subsequently, the driver delivers the combined invoice and barcoded card or sheet to the provider. This eliminates the need to hand-write delivery information.

In an alternative or in addition, information from the barcoded card may be scanned at the delivery location. Furthermore, the barcode could also be associated with the packaging (plastic bag) of the product, instead of a card or information sheet.

4.4 Integration of Inventory and Billing Systems

Figure 9:
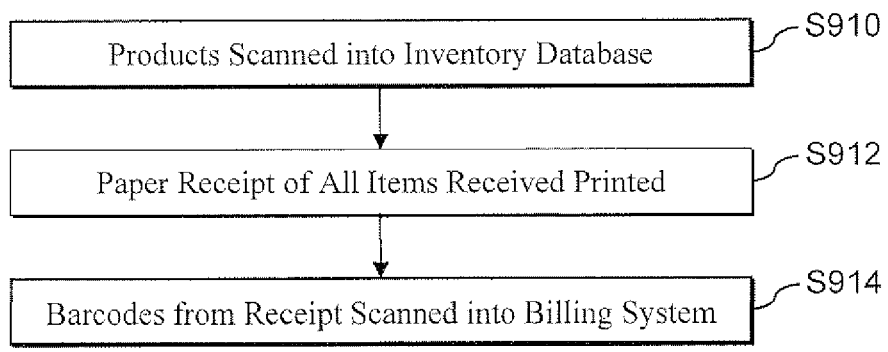
FIG. 9 is a flowchart of an exemplary process for integrating an inventory database with a billing system by using barcodes associated with products.

FIG. 9 is a flowchart of an exemplary process for integrating an inventory database with a billing system by using barcodes associated with products. This process is advantageous over conventional methods of billing because, for example, it saves a great amount of time compared to typing, it enhances accuracy by using barcodes, etc. Briefly, in step S910, products are scanned into the inventory database. It will be appreciated that any of the methods for building the inventory database disclosed herein may be used. After the items are entered into the database, a paper receipt of the items received into inventory is printed in step S912. In certain example embodiments, all items currently in inventory may be printed, while in other example embodiments only new items may be printed. Preferably, the printed receipt will include both a human-readable serial number and an associated barcode. Additional information, such as, for example, lot number, brief product name and/or description, etc. also may be printed, depending on the specific embodiment implemented. In step S914, barcodes from the receipt may be scanned into a billing system. Step S914 may occur when a product is dispensed (for example, to track who is receiving what products at which prices, etc.), or immediately after receiving products into inventory (for example, to define the scope of the products available for sale, rental, etc.). This function preferably integrates with a software "Received from Supplier" function, for example, to update inventory information.

It will be appreciated that the term "provider" has been used throughout this disclosure as a generic term. As such, the term "provider" should not be seen as limiting the embodiments to locating particular equipment at particular places. On the contrary, the term "provider" encompasses such entities as sleep labs, physicians' offices, distributors' warehouses, etc.

It also will be appreciated that the barcodes of the example embodiments described herein could be substituted by or used in conjunction with any other machine readable product identification means.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments.

What is claimed is:

1. A system for managing the treatment of patients diagnosed with sleep-disordered breathing and products used in their treatment, comprising:
    at least one barcode scanner configured to scan medically-prescribed barcodes to be used in identifying corresponding products and in retrieving identifying information about said identified products;
    an integrated product and patient database tangibly stored on a non-transitory computer readable storage medium, the integrated product and patient database being configured to store said retrieved identifying product information and information about patients; and,
    said product and patient database being updated at least when said products are received and dispensed as the medically-prescribed barcodes are scanned, the product and patient database being updated to include either or both of: (a) an automatically-generated reminder specific to a patient and product, the reminder including a date/time and a reason for the reminder, and (b) a rental and/or loaner agreement specific to the product.

2. The system of claim 1, further comprising a plurality of barcode scanners configured to scan said products and retrieve identifying information about said products.

3. The system of claim 2, further comprising a plurality of software applications running on a plurality of computer terminals.

4. The system of claim 3, wherein the plurality of software applications includes:
    a first application running on a computer terminal configured to access said product and patient database; and,
    a second application running on a remote device configured to access said product and patient database;
    wherein said product and patient database updates are shown in said first application and said second application.

5. The system of claim 4, wherein updates to said product and patient database by said second application are shown in said first application.

6. The system of claim 5, wherein said remote device is a computer.

7. The system of claim 5, wherein said remote device is a PDA.

8. The system of claim 2, wherein individual ones of said plurality of barcode scanners are located in at least two different locations.

9. The system of claim 1, wherein the barcode scanner is a wireless barcode scanner; and
    wherein said retrieved identifying product information is stored to said product and patient database through a communications network.

10. The system of claim 9, further comprising a processor for manipulating said retrieved identifying product information before storing said retrieved identifying product information to said product and patient database.

11. The system of claim 10, wherein said communications network is a cellular network.

12. The system of claim 11, wherein said retrieved identifying product information is transmitted over a data connection of said cellular network.

13. The system of claim 1, wherein information not contained in the identifying product information is stored to the product and patient database.

14. The system of claim 13, wherein said information not contained in the identifying product information comprises a note associated with a patient and/or product.

15. A method for managing the treatment of patients diagnosed with sleep-disordered breathing and products used in their treatment, said method comprising:
    scanning medically-prescribed barcodes associated with said products to retrieve identifying information about said products;
    storing said retrieved identifying product information and information about patients in an integrated product and patient database tangibly stored on a non-transitory computer readable storage medium;
    updating said product and patient database via at least one processor at least when said products are received and dispensed as the medically-prescribed barcodes are scanned so as to include either or both of: (a) an automatically-generated reminder specific to a patient and product, the reminder including a date/time and a reason for the reminder, and (b) a rental and/or loaner agreement specific to the product.

16. The method of claim 15, wherein said retrieved identifying product information is communicated over a communications network.

17. The method of claim 16, further comprising manipulating said retrieved identifying product information before storing said retrieved identifying product information to said product and patient database.

18. The method of claim 17, wherein said communications network is a cellular network.

19. The method of claim 18, wherein said retrieved identifying product information is transmitted over a data connection of said cellular network.

20. The method of claim 16, wherein the scanning step is performed by a plurality of scanners.

21. The method of claim 20, wherein individual ones of the plurality of barcode scanners are located in at least two different locations.

22. The method of claim 16, further comprising using a plurality of software applications running on a plurality of computer terminals.

23. The method of claim 15, further comprising storing to the product and patient database information not contained in the identifying product information.

24. The method of claim 23, further comprising creating a note associated with a patient and/or product.

* * * * *